US010718773B2

(12) United States Patent
Hanks et al.

(10) Patent No.: US 10,718,773 B2
(45) Date of Patent: Jul. 21, 2020

(54) IMMUNOHISTOCHEMISTRY SCORING METHODS AND COMPOSITIONS

(71) Applicant: Agilent Technologies, Inc., Santa Clara, CA (US)

(72) Inventors: Debra Hanks, Carpinteria, CA (US); Mai Nguyen, Ventura, CA (US); Marko Srdanov, Santa Barbara, CA (US); Che Hutson, Los Angeles, CA (US)

(73) Assignee: AGILENT TECHNOLOGIES, INC., Santa Clara, CA (US)

( * ) Notice: Subject to any disclaimer, the term of this patent is extended or adjusted under 35 U.S.C. 154(b) by 391 days.

(21) Appl. No.: 15/423,435

(22) Filed: Feb. 2, 2017

(65) Prior Publication Data

US 2017/0285029 A1    Oct. 5, 2017

Related U.S. Application Data

(60) Provisional application No. 62/317,177, filed on Apr. 1, 2016.

(51) Int. Cl.
*G01N 33/574* (2006.01)
*G16H 50/20* (2018.01)

(52) U.S. Cl.
CPC . *G01N 33/57407* (2013.01); *G01N 33/57492* (2013.01); *G16H 50/20* (2018.01); *G01N 2333/70517* (2013.01); *G01N 2333/70596* (2013.01); *G01N 2800/52* (2013.01)

(58) Field of Classification Search
None
See application file for complete search history.

(56) References Cited

PUBLICATIONS

Chung et al. Safety, PD-L1 expression, and clinical activity of avelumab (MSB0010718C), an anti-PD-L1 antibody, in patients with advanced gastric or gastroesophageal junction cancer.Journal of Clinical Oncology, 34(4), suppl. 167, Feb. 1, 2016.*
Broderick, Jason. (OncLive, pp. 1-3, published Nov. 28, 2017).*
Chakravarti, et al., "Predictive factors of activity of anti-programmed death-1/programmed death ligand-1 drugs: immunohistochemistry analysis", Transl Lung Cancer Res., 2015, 4(6):743-751.
Padda, et al., "Diffuse High Intensity PD-L1 Staining in Thymic Epithelial Tumors", J Thorac Oncol., 2015, 10(3):500-508.
Parker, et al., "Development and Evaluation of BioScore: A Biomarker Panel to Enhance Prognostic Algorithms for Clear Cell Renal Cell Carcinoma", Cancer, 2009, 115(10): 2092-2103.
Phillips, et al., "Development of an Automated PD-L1 Immunohistochemistry (IHC) Assay for Non-Small Cell Lung Cancer", Appl Immunohistochem Mol Morphol, 2015, 23(8):541-549.
Tarhini, et al., "Tumor associated PD-L1 expression pattern in!microscopically tumor positive sentinel lymph nodes in patients with melanoma", J Transl Med, 2015, 13:319. doi: 10.1186/s12967-015-0678-7.

* cited by examiner

*Primary Examiner* — Alana Harris Dent

(57) ABSTRACT

Aspects of the present disclosure provide methods for determining the eligibility of a subject having a malignancy for treatment with an anti-PD therapeutic agent. In certain embodiments, the method includes determining, by immunohistochemistry, the number of PD-L1 positive malignant cells in a tumor tissue section as well as the number of infiltrating non-malignant cells and/or non-malignant cells of the stromal interface area. The infiltrating non-malignant cells and/or non-malignant cells of the stromal interface area are positive for a marker selected from PD-L1, CD8, CD68, and any combination thereof. Compositions and kits or performing the disclosed methods are also provided.

17 Claims, 9 Drawing Sheets

RCC Correlation Table

|  | Total % PDL1 Positivity | PD-L1 % Positive NMC of SIA | CD8 % Positive Infilt NMC | CD8 % Positive NMC of SIA | CD68 % Positive NMC of SIA |
|---|---|---|---|---|---|
| Total % PDL1 Positivity | 1 | -0.07206 | 0.18382 | 0.09038 | -0.0449 |
| PD-L1 % Positive NMC of SIA |  | 1 | -0.00158 | 0.69463 | 0.8284 |
| CD8 % Positive Infilt NMC |  |  | 1 | 0.21514 | -0.10356 |
| CD8 % Positive NMC of SIA |  |  |  | 1 | 0.68936 |
| CD68 % Positive NMC of SIA |  |  |  |  | 1 |

Fig. 8

OC - Correlation Table

| | PDL1.1 | PDL1.3 | PDL1.4 | CD8.1 | CD8.2 | CD68.1 | CD68.2 |
|---|---|---|---|---|---|---|---|
| PDL1.1 | 1 | 0.028 | 0.081 | 0.326 | 0.171 | 0.096 | 0.128 |
| PDL1.3 | | 1 | 0.427 | 0.444 | 0.314 | 0.458 | 0.075 |
| PDL1.4 | | | 1 | 0.220 | 0.411 | 0.232 | 0.530 |
| CD8.1 | | | | 1 | 0.501 | 0.415 | 0.233 |
| CD8.2 | | | | | 1 | 0.249 | 0.644 |
| CD68.1 | | | | | | 1 | 0.138 |
| CD68.2 | | | | | | | 1 |

Key
PDL1.1   % Pos. malignant cells
PDL1.3   % Pos. infiltrating, non-malignant cells
PDL1.4   % Pos. non-malignant cells of the stromal interface area
CD8.1    % Pos. avg. highest infiltrating, non-malignant cells
CD8.2    % Pos. avg. highest non-malignant cells of stromal interface area
CD68.1   % Pos. avg. highest infiltrating, non-malignant cells
CD68.2   % Pos. avg. highest non-malignant cells of stromal interface area

Fig. 9

IMMUNOHISTOCHEMISTRY SCORING METHODS AND COMPOSITIONS

CROSS-REFERENCING

This application claims the benefit of provisional application Ser. No. 62/317,177, filed on Apr. 1, 2016, which application is incorporated by reference herein in its entirety.

BACKGROUND

Programmed cell death 1 ligand 1 (PD-L1) expression is implicated in evasion of immune responses involved in many contexts, including suppression of anti-tumor immune activity. PD-L1 expression has been shown in situ on a wide variety of solid tumors including breast, lung, colon, ovarian, melanoma, bladder, liver, salivary, stomach, gliomas, thyroid, thymic epithelial, head, and neck (Brown J A et al., 2003. J. Immunol. 170:1257-66; Dong H et al. 2002. Nat. Med. 8:793-800; Hamanishi J, et al. 2007. Proc. Natl. Acad. Sci. USA 104:3360-65; Strome S E et al. 2003. Cancer Res. 63:6501-5; Inman B A et al. 2007. Cancer 109:1499-505; Konishi J et. al. 2004. Clin. Cancer Res. 10:5094-100; Nakanishi J et. al. 2007. Cancer Immunol. Immunother. 56:1173-82; Nomi T et al. 2007. Clin. Cancer Res. 13:2151-57; Thompson R H et al. 2004. Proc. Natl. Acad. Sci. USA 101:17174-79; Wu C, Zhu Y, Jiang J, Zhao J, Zhang X G, Xu N. 2006. Acta Histochem. 108:19-24). In addition, PD-1 expression can be upregulated on tumor infiltrating lymphocytes (TILs), and this may also contribute to tumor immunosuppression (Blank C et al. 2003. J. Immunol. 171:4574-81).

In ovarian cancer, PD-L1 expression is inversely correlated with intraepithelial, but not stromal, infiltrating CD8 T cells, suggesting that PD-L1 inhibits the intratumor migration of CD8 T cells (Hamanishi J et. al. 2007. Proc. Natl. Acad. Sci. USA 104:3360-65). Translation of PD-L1 mRNA is enhanced by loss of PTEN and the ensuing activation of Akt, a common event in tumorigenesis (Parsa A T et al. 2007. Nat. Med. 13:84-88). Studies relating PD-L1 expression on tumors to disease outcome show that PD-L1 expression strongly correlates with unfavorable prognosis in kidney, ovarian, bladder, breast, gastric, and pancreatic cancer (Hamanishi J et al. 2007. Proc. Natl. Acad. Sci. USA 104:3360-65; Inman B A et al. 2007. Cancer 109:1499-505; Konishi J et. al. 2004. Clin. Cancer Res. 10:5094-100; Nakanishi J et. al. 2007. Cancer Immunol. Immunother. 56:1173-82; Nomi T et al. 2007. Clin. Cancer Res. 13:2151-57; Thompson R H et al. 2004. Proc. Natl. Acad. Sci. USA 101:17174-79; Wu C, Zhu Y, Jiang J, Zhao J, Zhang X G, Xu N. 2006. Acta Histochem. 108:19-24). In addition, these studies suggest that higher levels of PD-L1 expression on tumors may facilitate advancement of tumor stage and invasion into deeper tissue structures. Studies in animal models demonstrate that PD-L1 on tumors inhibits T cell activation and lysis of tumor cells and in some cases leads to increased tumor-specific T cell death (Dong H et al. 2002. Nat. Med. 8:793-800; Hirano F et al. 2005. Cancer Res. 65:1089-96).

Non-malignant cells have also been implicated in playing important roles in tumor maintenance and growth. For example, tumor-associated APCs can utilize the PD-1:PD-L pathway to control antitumor T cell responses (Curiel et al. 2003. Nat. Med. 9:562-67). In this study, PD-L1 expression on a population of tumor-associated myeloid DCs was shown to be up-regulated by tumor environmental factors.

Given the role PD-1/PD-L1 plays in tumor biology, therapeutic agents that target this molecule have been of significant interest. Indeed, anti-PD-1/PD-L1 therapy (or anti-PD therapy) has generated significant clinical benefits by inducing regression of advanced and metastatic tumors and improving survival. Anti-PD therapy can have durable effects, tolerable toxicity, and is applicable to a broad spectrum of cancer types, especially in solid tumors.

Examples of anti-PD therapeutics currently in use or in development include the following:

Nivolumab, Bristol-Myers Squibb (also known as Opdivo, MDX-1106, BMS-936558, and ONO-4538), was the first mAb targeting PD-1 to show significant clinical activity in unresectable or metastatic melanomas, non-small-cell lung carcinoma (NSCLC), and metastatic renal cell carcinomas.

Pembrolizumab, Merck (also known as Keytruda, lambrolizumab, and MK-3475), is an Anti-PD-1 monoclonal antibody that has shown similar efficacy and safety compared with nivolumab in a phase I clinical trial in advanced melanoma (NCT01295827) and is now an FDA-approved second-line drug for the treatment of melanoma. Pembrolizumab is also effective in patients with advanced NSCLC and has shown promising effects in other solid tumors, including advanced gastric cancer, advanced bladder cancer, head and neck cancer, classical Hodgkin's lymphoma, and triple-negative breast cancer.

BMS-936559, Bristol-Myers Squibb (also known as MDX-1105) is a fully human IgG4 anti-PD-L1 mAb that inhibits the binding of the PD-L1 ligand to both PD-1 and CD80 and has demonstrated therapeutic efficacy in a phase I clinical trial (NCT00729664).

MPDL3280A, Genentech/Roche, is an engineered anti-PD-L1 IgG1 mAb that can inhibit PD-L1 interactions with both PD-1 and B7-1. A study of metastatic urothelial bladder cancer (UBC) demonstrated that MPDL3280A has marked activity in controlling tumor growth. Moreover, owing to the mild side effects, including a lack of renal toxicity, patients with UBC, who are often older and have a higher incidence of renal impairment, are thought to tolerate MPDL3280A better than chemotherapy (NCT01375842). In an expansion phase I trial across multiple cancer types, including NSCLC, melanoma, renal cell carcinoma, and other tumors, responses to MPDL3280A were observed in patients with tumors expressing high levels of PD-L1, especially when PD-L1 was expressed by tumor infiltrating lymphocytes TILs.

Pidilizumab (Medivation/CureTech), MEDI4736 (AstraZeneca), and Avelumab (MSB0010718C; Merck-Sorono) are additional PD-L1 targeting antibody-based therapeutic agents that show promise in the treatment of multiple human cancers.

In addition to developing anti-PD therapeutic agents, work in this area has included performing more detailed analysis of not only the malignant cells in tumor biopsies, but also non-malignant cells to identify patients who may respond to these therapies.

In this regard, Sato et al. (2005. PNAS 102(51), 18538-18543) quantified TILs in tumor sections by microscopy and found that the subgroup with the lowest frequency of intraepithelial CD8 TILs consistently showed poorer survival by univariate and multivariate analysis. Stumpf et al. (2009. Br J Cancer, 101(9), 1513-1521) characterized the presence and exact localization of TILs by IHC in a homogeneous group of 100 serous FIGO stage III ovarian carcinoma patients treated by different adjuvant chemotherapy protocols and found that intraepithelial CD8-positive T lymphocytes were correlated with improved overall survival (OS) in all optimally debulked patients and in those undergoing paclitaxel/carboplatin therapy. Tumeh et al. (2014. Nature, 515(7528), 568-571) analyzed samples from 46 patients with metastatic melanoma obtained before and during anti-PD-1 therapy (pembrolizumab). They found that pre-treatment samples obtained from responding patients showed higher numbers of CD8-, PD-1- and PD-L1-expressing cells at the invasive tumor margin and inside tumors, with close proximity between PD-1 and PD-L1. They also reported that during treatment, tumors exhibited a parallel increase in CD8-cell density at both the invasive margin and tumor centre in the response group. Taube et al. (2014. Clinical Cancer Research, 20(19), 5064-5074) reported on a study of pretreatment tumor specimens from patients with melanoma, non-small cell lung carcinoma (NSCLC), renal cell carcinoma (RCC), colorectal carcinoma, or castration-resistant prostate cancer who had been treated on an early-phase trial of anti-PD-1 (nivolumab). Immunoarchitectural features, including PD-1, PD-L1, and PD-L2 expression, patterns of immune cell infiltration, and lymphocyte subpopulations, were assessed for interrelationships and potential correlations with clinical outcomes. Among other findings, Taube et al. found that tumor cell PD-L1 expression correlated with objective response to anti-PD-1 therapy and that these correlations were stronger than borderline associations of PD-1 expression or the presence of intratumoral immune cell infiltrates with response.

While progress has been made in this area, there is still a need to improve methods for identifying patients that will respond effectively to anti-PD therapy.

SUMMARY

Aspects of the present disclosure provide methods for determining the eligibility of a subject having a malignancy for treatment with an anti-PD therapeutic agent. In certain embodiments, the method includes determining, by immunohistochemistry (IHC), the number of PD-L1 positive malignant cells (MC) in a tumor tissue section as well as the number of infiltrating non-malignant cells (I-NMC) and/or non-malignant cells of the stromal interface area (NMC-SIA). In certain embodiments, The I-NMC and/or NMC-SIA are positive for a marker selected from PD-L1, CD8, CD68, and any combination thereof, e.g., as visualized using IHC. The values obtained/determined for these parameters is used to generate an eligibility score, where the eligibility score is used to determine eligibility of a subject for therapeutic treatment with an anti-PD therapeutic agent, e.g., an anti-PD/PD-L1 antibody. Compositions and kits for performing the methods are also provided.

BRIEF DESCRIPTION OF THE FIGURES

Certain aspects of the following detailed description are best understood when read in conjunction with the accompanying drawings. It is emphasized that, according to common practice, the various features of the drawings are not to scale. On the contrary, the dimensions of the various features are arbitrarily expanded or reduced for clarity. Included in the drawings are the following figures:

FIG. 8. RCC Correlation table that summarizes relationships between markers and regions of interest. Red font highlights moderate (0.69) and strong (0.83) correlations.

FIG. 9. OC Correlation Table, summarizes the relationships between markers and regions of interest. The strongest correlation is (0.664) between CD8 and CD68 for the non-malignant cells of the stromal interface.

DEFINITIONS

Figure 1:
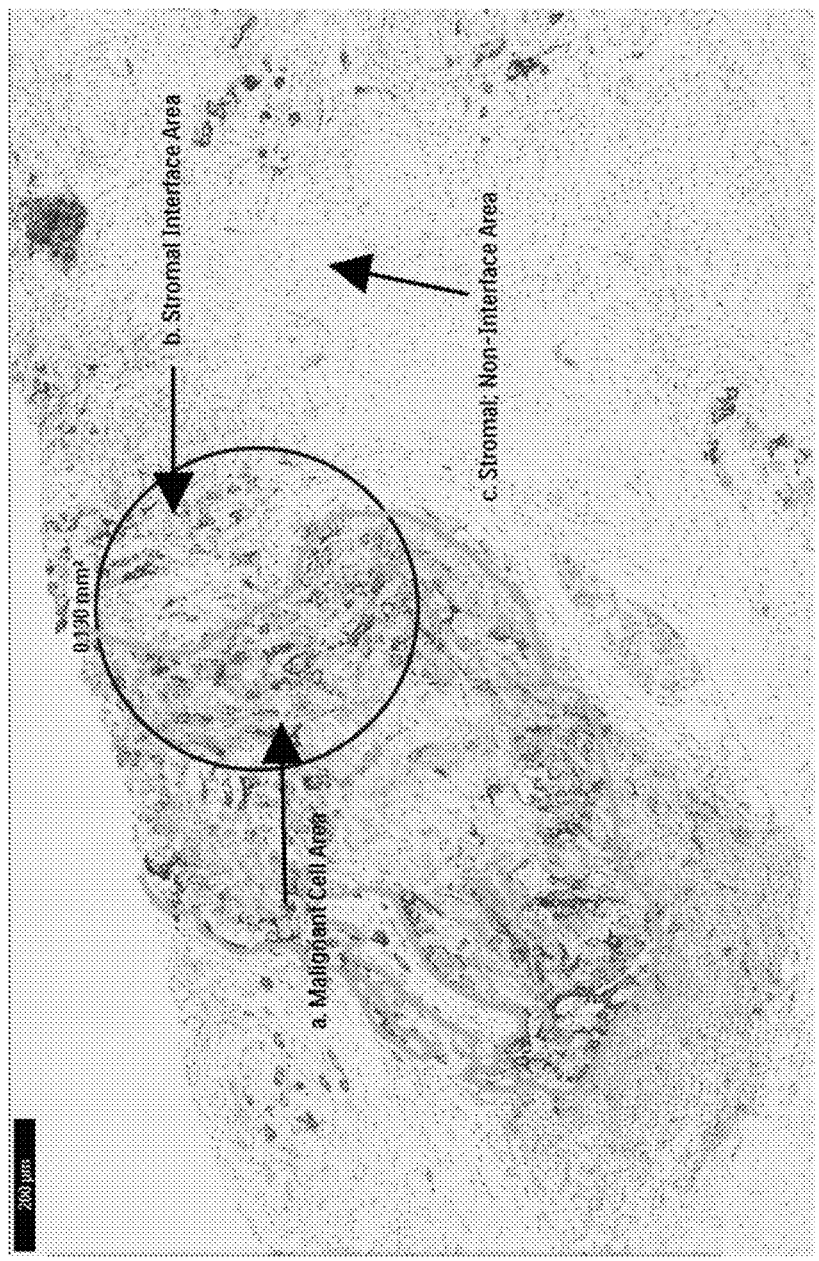
FIG. 1: A Conceptual Image of Scoring Regions (0.190 mm2 blue circle above, approximates a 40× field on a microscope): a. Malignant Cells—neoplastic cells with abnormal morphology. b. Stromal Interface—stroma adjacent to malignant cells. c. Stromal Non-Interface—stroma not involved with malignant cells. Blue Circle—The field of view with ½ field of view with Malignant Cell Area and remaining ½ of field of view as Stromal Interface. The Malignant Cell margin (green line) should approximate half the field of view.

Unless defined otherwise herein, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

All patents and publications, including all sequences disclosed within such patents and publications, referred to herein are expressly incorporated by reference.

Numeric ranges are inclusive of the numbers defining the range. Unless otherwise indicated, nucleic acids are written left to right in 5' to 3' orientation; amino acid sequences are written left to right in amino to carboxy orientation, respectively.

The headings provided herein are not limitations of the various aspects or embodiments of the invention. Accordingly, the terms defined immediately below are more fully defined by reference to the specification as a whole.

Unless defined otherwise, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Markham, THE HARPER COLLINS DICTIONARY OF BIOLOGY, Harper Perennial, N.Y. (1991) provide one of skill with the general meaning of many of the terms used herein. Still, certain terms are defined below for the sake of clarity and ease of reference.

The term "PD-L1" refers to the Programmed cell death ligand 1 molecule. PD-L1 may refer to human PD-L1 or homologs in other organisms, depending on the context in which it is used. Human PD-L1 is also known as CD274, B7-H, B7H1, B7-H1, B7 homolog 1, MGC142294, MGC142296, PDCD1L1, PDCD1LG1, PDCD1 ligand 1, PDL1, Programmed cell death 1 ligand 1 and Programmed death ligand 1 and has Uniprot number Q9NZQ7 and NCBI gene ID number 29126. Human PD-L1 is a 290 amino acid type I transmembrane protein encoded by the CD274 gene on human chromosome 9. Mouse PD-L1 has NCBI GenBank ID number ADK70950.1.

A "diagnostic marker" is a specific biochemical in the body which has a particular molecular feature that makes it useful for detecting a disease, measuring the progress of disease or the effects of treatment, or for measuring a process of interest.

The term "epitope" as used herein is defined as small chemical groups on the antigen molecule that is bound to by an antibody. An antigen can have one or more epitopes. In many cases, an epitope is roughly five amino acids or sugars in size. One skilled in the art understands that generally the overall three-dimensional structure or the specific linear sequence of the molecule can be the main criterion of antigenic specificity.

A "subject" of diagnosis or treatment is a plant or animal, including a human. Non-human animals subject to diagnosis or treatment include, for example, livestock and pets.

As used herein, the term "tissue section" refers to a piece of tissue that has been obtained from a subject, fixed, sectioned, and mounted on a planar surface, e.g., a microscope slide. A "tumor tissue sample" includes cells derived from a tumor in a subject, e.g., a human subject having a malignancy.

As used herein, the term "formalin-fixed paraffin embedded (FFPE) tissue section" refers to a piece of tissue, e.g., a biopsy that has been obtained from a subject, fixed in formaldehyde (e.g., 3%-5% formaldehyde in phosphate buffered saline) or Bouin solution, embedded in wax, cut into thin sections, and then mounted on a planar surface, e.g., a microscope slide.

As used herein, the term "resin embedded tissue section" refers to a piece of tissue, e.g. a biopsy that has been obtained from a subject, fixed, (e.g in 3-5% glutaraldehyde in 0.1M phosphate buffer), dehydrated, infiltrated with epoxy or methacrylate resin, cured, cut into thin sections, and then mounted on a planar surface, e.g., a microscope slide.

As used herein, the term "cryosection" refers to a piece of tissue, e.g. a biopsy that has been obtained from a subject, snap frozen, embedded in optimal cutting temperature embedding material, frozen, cut into thin sections and fixed (e.g. in methanol or paraformaldehyde) and mounted on a planar surface, e.g., a microscope slide.

The term "staining" includes binding a target (e.g., an antigen) in a planar cellular sample (e.g., a tissue section) with a target-specific binding agent (e.g., an antibody or a nucleic acid) and then detecting the presence of the target-specific binding agent on the planar cellular sample using a detectable label (or chromogen). The detectable label can be directly conjugated to the target-specific binding agent (e.g., a primary antibody) or may be conjugated to a secondary reagent that binds specifically to an unlabeled target-specific reagent (e.g., a secondary antibody). In some cases, the target-specific reagent is itself detectable, and thus no additional attached label is needed.

A "chromogen" or "chromogenic compound" and the like is a substance that can be converted into a colored compound under specific conditions, e.g., when acted upon by an enzyme or under specific chemical/reaction conditions. Examples of enzyme-substrate combinations include: (i) Horseradish peroxidase (HRP) with hydrogen peroxidase as a substrate, where the hydrogen peroxidase oxidizes a dye precursor [e.g., orthophenylene diamine (OPD) or 3,3',5,5'-tetramethyl benzidine hydrochloride (TMB)]; (ii) alkaline phosphatase (AP) with para-Nitrophenyl phosphate as chromogenic substrate; and (iii) β-D-galactosidase (β-D-Gal) with a chromogenic substrate (e.g., p-nitrophenyl-β-D-galactosidase) or fluorogenic substrate (e.g., 4-methylumbelliferyl-β-D-galactosidase). Numerous other enzyme-substrate combinations are available to those skilled in the art. For a general review of these, see U.S. Pat. Nos. 4,275,149 and 4,318,980.

As used herein, the term "target-specific binding agent" means any agent that specifically binds to a target or analyte of interest, e.g., a target of interest that is present in a tissue section as described herein (e.g., a polypeptide or polynucleotide). Examples of target-specific binding agents include antibodies, receptors, and ligands, or target-binding fragments thereof, polynucleotide probes, and the like.

As used herein, the term "multiplexing" refers to using more than one label, stain, and/or chromogen for the simultaneous or sequential detection and measurement of a target in a sample, e.g., a tissue section.

As used herein, the terms "antibody" and "immunoglobulin" are used interchangeably and are well understood by those in the field. Those terms refer to a protein consisting of one or more polypeptides that specifically binds an antigen. One form of antibody constitutes the basic structural unit of an antibody. This form is a tetramer and consists of two identical pairs of antibody chains, each pair having one light and one heavy chain. In each pair, the light and heavy chain variable regions are together responsible for binding to an antigen, and the constant regions are responsible for the antibody effector functions. These terms also include fragments of antibodies which retain specific binding to antigen or target, including, but not limited to, Fab, Fv, scFv, and Fd fragments, chimeric antibodies, humanized antibodies, single-chain antibodies, bi-specific hybrid antibodies, and fusion proteins comprising an antigen-binding portion of an antibody and a non-antibody protein. See, e.g., Hood et al., "Immunology", Benjamin, N.Y., 2nd ed. (1984); Hunkapiller and Hood, Nature, 323, 15-16 (1986); Lanzavecchia et al., Eur. J. Immunol. 17, 105-111 (1987); Huston et al., Proc. Natl. Acad. Sci. U.S.A., 85, 5879-5883 (1988); and Bird et al., Science, 242, 423-426 (1988) which are hereby incorporated by reference herein in their entirety.

As used herein, the terms "primary antibody" and "secondary antibody" refer to different antibodies, where a primary antibody is a polyclonal or monoclonal antibody from one species (rabbit, mouse, goat, donkey, etc.) that specifically recognizes an antigen (e.g., a biomarker) in a sample (e.g., a human tissue sample) under study, and a secondary antibody is an antibody (usually polyclonal) from a different species that specifically recognizes the primary antibody, e.g., in its Fc region.

Sometimes, the label may be indirectly conjugated with the antibody. The skilled artisan will be aware of various techniques for achieving this. For example, the antibody can be conjugated with biotin and any of the four broad categories of labels mentioned above can be conjugated with avidin, or vice versa. Biotin binds selectively to avidin and thus, the label can be conjugated with the antibody in this indirect manner. Alternatively, to achieve indirect conjugation of the label with the antibody, the antibody may be conjugated with a small hapten and one of the different types of labels mentioned above is conjugated with an anti-hapten antibody. Thus, indirect conjugation of the label with the antibody can be achieved. In some embodiments of the invention one or more secondary antibody molecules may be conjugated with a label-conjugated polymer backbone. Thus, amplification of the signal may be achieved.

Indirectly and directly labeled secondary antibodies are also commercially available. For example, one example of commercially available label-conjugated polymer backbone carrying secondary antibody molecules reagent is EnVision™ reagent (DAKO). A secondary antibody carrying a label aimed for a particular type of detection may be obtained from numerous manufacturers.

The term "specific binding" refers to the ability of a binding agent to preferentially bind to a particular analyte that is present in a homogeneous mixture of different analytes. In certain embodiments, a specific binding interaction will discriminate between desirable and undesirable analytes in a sample, in some embodiments more than about 10 to 100-fold or more (e.g., more than about 1000- or 10,000-fold).

In certain embodiments, the affinity between a binding agent and analyte when they are specifically bound in a capture agent/analyte complex is characterized by a KD (dissociation constant) of less than 10-6 M, less than 10-7 M, less than 10-8 M, less than 10-9 M, less than 10-10 M, less than 10-11 M, or less than about 10-12 M or less.

A "plurality" contains at least 2 members. In certain cases, a plurality may have at least 10, at least 100, at least 1000, at least 10,000, at least 100,000, at least 106, at least 107, at least 108 or at least 109 or more members.

Other definitions of terms may appear throughout the specification.

DETAILED DESCRIPTION

In order to further illustrate the present invention, the following specific examples are given with the understanding that they are being offered to illustrate the present invention and should not be construed in any way as limiting its scope.

As summarized above, aspects of the present disclosure include methods for determining the eligibility of a subject having a malignancy for treatment with an anti-PD therapeutic agent. In certain embodiments, the method includes: determining the percentage PD-L1 positive malignant cells (MC) per total malignant cells (TMC) (% MC/TMC) in a tumor tissue section from the subject; and determining a second parameter of a tumor tissue section from the subject, where the second parameter is selected from: (i) the percentage of infiltrating non-malignant cells (I-NMC) per TMC (% I-NMC/TMC); and (ii) the percentage of non-malignant cells of the stromal interface area (NMC-SIA) per TMC (% NMC-SIA/TMC). In certain embodiments, the I-NMC and NMC-SIA are positive for a marker selected from PD-L1, CD8, CD68, and any combination thereof. These parameters are employed to determine whether the subject is eligible for treatment with an anti-PD therapeutic agent, e.g., by calculating an eligibility score.

Determining the percentage PD-L1 positive cells, CD8 positive cells, and/or CD68 positive cells can be done in any convenient manner, for example by immunohistochemistry (IHC) staining, in-situ hybridization (ISH), histological stain, and combinations thereof. In certain embodiments, the tumor tissue section is analyzed by IHC. Where multiple targets are assessed, e.g., a combination PD-L1, CD8 and/or CD68, the IHC may be done in a multiplex fashion, i.e., all markers assessed on the same tissue section simultaneously (e.g., using detectably distinguishable target-specific binding agents), or in separate tissue sections derived from the same tumor biopsy from the subject.

In certain additional embodiments, the method further includes staining the tissue section for at least one (or multiple) additional targets or with a stain. In some embodiments, the stain is a histological stain, including but not limited to hematoxylin and eosin (H&E stain), which is the most commonly used light microscopy stain in histology and histopathology. Hematoxylin, a basic dye, stains nuclei blue due to an affinity to nucleic acids in the cell nucleus; eosin, an acidic dye, stains the cytoplasm pink. Another commonly performed histochemical technique is the Perls Prussian blue reaction, used to demonstrate iron deposits in diseases like hemochromatosis. There are many other staining techniques known in to those of skill in the art that can be used to selectively stain cells and cellular components that find use in the present disclosure, and as such no limitation in this regard is intended.

The staining of a target (e.g., PD-L1, CD8, and/or CD68) in the tissue section is generally done by contacting the tissue section with one or more target-specific binding agents under suitable conditions to allow for binding of the target-specific binding agent to its desired target (while minimizing non-target binding). As noted above, the term "target-specific binding agent" means any agent that specifically binds to a target or analyte of interest, e.g., a target of interest that is present in a tissue section as described herein (e.g., a polypeptide or polynucleotide). In some embodiments, the target-specific binding agent is an antibody (or target-binding fragments thereof), e.g., as used in IHC. An IHC method may be performed with primary and secondary antibodies or without using secondary antibodies (e.g., where the primary antibody is detectably labeled). In certain other embodiments, the target-specific binding agent is a nucleic acid or nucleic acid binding agent, e.g., as employed in in situ hybridization (ISH) reactions. For example, the target binding reagent can be a DNA, RNA, DNA/RNA hybrid molecule, peptide nucleic acid (PNA), and the like. No limitation in the metes and bounds of a target-specific binding agent that finds use in the subject disclosure is intended.

The target-specific binding agent (or any secondary reagent used to detect the target-specific binding agent) may be attached to any suitable detectable label (or chromogen) or enzyme capable of producing a detectable label. Thus, in certain embodiments, the first or second label is produced by an enzymatic reaction, e.g., by the activity of horseradish peroxidase, alkaline phosphatase, and the like. Any convenient enzymatic label/chromogen deposition system can be employed, and as such, no limitation in this regard is intended. The term "detectably labeled" includes both of these configurations.

In some embodiments, for example where the staining is done by IHC, the staining reagents used may include one or more antibodies that each bind to a different antigen. For example, a set of antibodies may include a first antibody that binds to a first antigen, a second antibody that binds to a second antigen, a third antibody that binds to a third antigen and, optionally a fourth antibody that binds to a fourth antigen and/or further antibodies that bind to further antigens. In some embodiments, the antibodies used are primary antibodies that are detected by use of a secondary antibody (or other reagent). The staining steps thus may be done by incubating the tissue section with the primary antibodies and then, after the primary antibody has bound to the tissue section, incubating the tissue section with the labeled secondary antibodies (as is done in standard IHC protocols). In some embodiments, each of the primary antibodies is from a different species (e.g., goat, rabbit, mouse, camel, chicken, donkey, etc.) and the corresponding secondary antibodies are distinguishably labeled from each other.

In some embodiments, the first and second (and subsequent) targets being detected in are different from each other, e.g., are different proteins or polynucleotides (e.g., different genes). However, in some embodiments, there may be some overlap. For example, in certain cases, a first target-specific binding agent may bind to the same target as a second target-specific binding agent but at a different epitope or site.

In certain embodiments, the tissue section is a formalin fixed and paraffin embedded (FFPE) tissue section. In alternative embodiments, the tissue section has been fixed in a different way, including tissue sections that have been fixed in, e.g., acrolein, glyoxal, smium tetroxide, arbodiimide, mercuric chloride, zinc salts, picric acid, potassium dichromate, ethanol, methanol, acetone, and/or acetic acid.

In certain embodiments, the method further comprises comparing the relative location of the detected first and second (or any subsequent) labels on the tissue section(s). This can be done, for example, by overlaying multiple images of the slide that were collected during the analysis (e.g., for different labels). For example, one or more images collected for the labels of a first tissue section (or first label) can be overlayed onto one or more images collected for a second adjacent tissue section (or second, distinguishable label).

In certain embodiments, the images may be overlaid and analyzed to identify the boundaries of individual cells or regions in the tissue section, histological compartments, and/or subcellular features in individual cells, in the image. Computer-implemented methods for segmenting images of cells and tissues are known in the art and range from relatively simple thresholding techniques (see, e.g., Korde et al. Anal Quant Cytol Histol. 2009 31: 83-89 and Tuominen et al. Breast Cancer Res. 2010 12: R56), to more sophisticated methods, such as, for instance, adaptive attention windows defined by the maximum cell size (Ko et al. J Digit Imaging. 2009 22: 259-274) or gradient flow tracking (Li, et al. J Microsc. 2008 231: 47-58). Some suitable image segmentation methods may be reviewed in Ko et al. (J Digit Imaging. 2009 22: 259-74) and Ong et al. (Comput Biol Med. 1996 26:269-79). Next the data that corresponds to each of the individual parameters that have been defined by the segmenting are integrated to provide, for each cell, values that indicate which markers are associated with the cell. In certain cases, a cell may be identified as being malignant, non-malignant, infiltrating non-malignant, etc., as a result of this analysis. This data may allow one to potentially type the cells in the sample. As such, this method may comprise displaying an image of the sample, in which the cells are color-coded by their type.

In certain embodiments, the tissue section may be a section of a tissue biopsy obtained from a patient, e.g., a patient having a malignancy. Biopsies of interest include both tumor and non-neoplastic biopsies of skin (melanomas, carcinomas, etc.), soft tissue, bone, breast, colon, liver, kidney, adrenal, gastrointestinal, pancreatic, gall bladder, salivary gland, cervical, ovary, fallopian tube, peritoneum, uterus, testis, prostate, lung, thymus, thyroid, parathyroid, pituitary (adenomas, etc.), brain, spinal cord, ocular, nerve, and skeletal muscle, etc. In certain embodiments, the subject from which the biopsy if obtained has a malignancy is selected from: renal cell carcinoma, urothelial carcinoma, ovarian carcinoma, myeloma, melanoma, lung cancer, squamous cell carcinoma, gastric cancer, bladder cancer, head and neck cancer, classical Hodgkin's lymphoma, Merkel cell carcinoma, and breast cancer.

In some embodiments, the method may involve obtaining one or more images as described above (e.g., an electronic form of which may have been stored in the memory of a database and retrieved either locally or forwarded from a remote location) and may be analyzed by a doctor or other medical professional to assess the eligibility of the subject for an anti-PD therapy using the eligibility scores described below. In such embodiments, the image need not be analyzed in real time. In other embodiments, the tissue sections are assessed in real time, i.e., not from a stored image of the slide. In some embodiments, a slide or image of the slide, as described above, is assessed in an automated fashion in silico, e.g., without the slide(s) or image(s) of the slide being assessed by a human. In such embodiments, the slide(s)/image(s) are analyzed by a computer that has been programmed to analyze the staining pattern and assess the eligibility of the subject for an anti-PD therapy using the eligibility scores described below.

In any embodiment, data can be forwarded to a "remote location," where "remote location" means a location other than the location at which the image is examined. For example, a remote location could be another location (e.g., office, lab, etc.) in the same city, another location in a different city, another location in a different state, another location in a different country, etc. As such, when one item is indicated as being "remote" from another, what is meant is that the two items can be in the same room but be separated, or at least in different rooms or different buildings, and can be at least one mile, ten miles, or at least one hundred miles apart. "Communicating" information references transmitting the data representing that information as electrical signals over a suitable communication channel (e.g., a private or public network). "Forwarding" an item refers to any means of getting that item from one location to the next, whether by physically transporting that item or otherwise (where that is possible) and includes, at least in the case of data, physically transporting a medium carrying the data or communicating the data. Examples of communicating media include radio or infra-red transmission channels as well as a network connection to another computer or networked device, and the internet or include email transmissions and information recorded on websites and the like. In certain embodiments, the image may be analyzed by an MD or other qualified medical professional, and a report based on the results of the analysis of the image may be forwarded to the patient from which the sample was obtained.

Specific Embodiment

In order to identify patients eligible for treatment with anti-PD therapy (e.g., Merck Serono/Pfizer's MSB0010718C immunotherapy), the PD-L1 IHC 73-10 pharmDx kit is used in conjunction with Dako's CD8 and CD68 antibodies to evaluate formalin-fixed, paraffin embedded (FFPE) tumor tissue from renal cell carcinoma (RCC), urothelial carcinoma (UC), or epithelial ovarian carcinoma (OC) specimens (Taube et al., 2013). The scoring guidelines used to evaluate these patients specimens is intended to be unique to any other product and provide enhanced eligibility criteria for RCC, UC and OC patients who will receive anti-PD treatment.

The 3-panel assessment includes scoring of the following antibodies:

PD-L1 exhibits a membranous and cytoplasmic expression pattern. Monoclonal Rabbit Anti-PD-L1, Clone MKP-1A-73-10 (7310) antibody predominantly stains the membrane and to a lesser degree the cytoplasm of the PD-L1 positive tumor cells. Cytoplasmic reactivity is expected to be strongest in cases with intensely stained membranes. Positivity in tumor cells is defined as circumferential or partial linear plasma membrane staining. Anti-PD-L1 antibody is known to stain both malignant and non-malignant cell types. Positivity in non-malignant cell types is defined as circumferential or partial linear plasma membrane staining.

CD8 Monoclonal Mouse Anti-Human CD8 Clone C8/144B is a transmembrane glycoprotein with a molecular mass of 68 kDa. It is expressed as a disulfide-linked heterodimer comprising a 32-34 kDa α- and a 30-32 kDa β-chain, or as a homodimer comprising two α-chains. Both CD8α and CD8β have a typical immunoglobulin variable region-like domain in an N-terminal extracellular portion that makes them members of the immunoglobulin gene superfamily. CD8 is expressed mostly as the ab heterodimer by a majority of thymocytes, and by class 1 major histocompatibility complex restricted, mature, suppressor/cytotoxic T cells. A proportion of gamma delta T cells and NK cells express the CD8 as a homodimer. This antibody labels cytotoxic/suppressor T cells and is useful for the identification of these cells and their neoplastic counterparts. Cells labeled by the antibody display membrane staining and is strongly reactive in the cytoplasm.

CD68 Monoclonal Mouse Anti-Human CD68 Clone PG-M1 is a highly glycosylated lysosomal membrane protein with an Mw of 110,000 Da. The CD68 protein belongs to a family of lysosomal glycoprotein (LGP)/plasma membrane shuttling proteins that play a role in endocytosis and/or lysosomal trafficking. CD68 is expressed strongly in cytoplasmic granules, and weakly on the surface of macrophages, monocytes, neutrophils, basophils and NK cells. Additionally, CD68 is expressed by approximately 40% of peripheral blood B cells and is weakly expressed in 50% of B-cell type acute lymphoblastic leukaemia (B-ALL) cells. CD68 can also be found in the cytoplasm of non-haematopoietic tissues, especially the liver, and renal glomeruli and tubules. Unlike many other CD leucocyte antigens, the CD68 molecule is antigenically very heterogenous, and different antibodies to CD68 show different cellular reactivities. CD68 stains cells of the monocyte/macrophage lineage labeled by the antibody display cytoplasmic (diffuse or granular) staining.

The following definitions are relevant to the description below:

1. Malignant Cells (MC): neoplastic cells exhibiting invasive or metastatic growth; cells that exhibit cytologic features of malignancy, synonymous with tumor cells (e.g. cellular pleomorphism, anisokaryosis, high or variable nuclear to cytoplasmic ratio, alteration of chromatin pattern, etc.).

2. Non-Malignant Cells (NMC): benign neoplasms; preneoplastic lesions; immune and stromal cells.

3. Stroma: connective tissue (fibroblasts, extra cellular matrix) and vessels, including tumor stroma, or stroma present within a neoplasm.

4. Interface: Region of interest (ROI) between malignant and non-malignant cell populations.

5. Stromal Interface Area (SIA): stroma adjacent to malignant cells.

6. Stromal Non-Interface: stroma not adjacent to malignant cells.

7. Infiltrating Non-Malignant Cells (I-NMC): Non-malignant cells within or between malignant cells with no intervening stroma.

8. Invasive margin of tumor: interface between tumor (including malignant cells and tumor stroma) and adjacent local (i.e. non-tumor) tissue; outer margin of tumor.

FIG. 1 provides a conceptual image of certain of the scoring regions of a tissue section as described herein. The 0.190 mm² blue circle in FIG. 1 approximates a 40× objective field on a standard histology microscope. Region (a) shows Malignant Cells, i.e., neoplastic cells with abnormal morphology. Region (b) shows a Stromal Interface Area (SIA), i.e., stroma adjacent to malignant cells. Region (c) shows Stromal Non-Interface region, i.e., stroma not involved with or adjacent to malignant cells. When the blue circle field of view is placed with its center positioned along the Malignant Cell margin (the green line), a first half of the field of view approximates the Malignant Cell Area (region (a)) and the other half of the field of view approximates the Stromal Interface Area (region (b)).

(1) PD-L1+ Malignant Cells (MC)

The tissue section is evaluated for the number of PD-L1-positive Malignant Cells (MC) exhibiting any staining intensity as a percentage of the Total Malignant Cells (TMC) present in the tissue section. Positive PD-L1 expression is defined as partial linear or circumferential staining of the plasma membrane between tumor cells (i.e. apical staining at lumen of tumor glands, basal staining at the interface of tumor cells with stroma and staining at the outer margin of dissociated tumor cells/cell clusters is not considered PD-L1+ tumor membrane staining).

The scores are recorded as actual percent PD-L1 positive malignant cells per total malignant cells (% MC/TMC).

Mark if any 3+ staining intensity is observed at 4×/5× as 'P=Present' or 'A=Absent'.

(2) Infiltrating Non-Malignant Cells (I-NMC)

(a) PD-L1 Positive: The tissue section is evaluated to estimate the number of positive Infiltrating Non-Malignant Cells (I-NMC) exhibiting any staining intensity as a percentage of the Total Malignant Cells (TMC). Weak staining in the matrix is considered background staining and only non-malignant cells staining at greater intensities should be considered positive.

The scores are recorded as actual percent positive, % I-NMC+/TMC.

Specimens with high percentage of PD-L1+MC may pose a challenge for determining the PD-L1 positive I-NMC percentage. In these cases, CD8 and CD68 can be used to estimate PD-L1 I-NMC score. 'Obscured PD-L1' can be recorded in Comments section to describe PD-L1+I-NMC obscured by highly positive MC. In highly positive specimens obscuring discrimination between malignant and non-malignant cells, an aggregate or total score can be recorded.

This score is not technically a true percentage, but rather a ratio. Thus, if an aggregate or total PD-L1+ score is calculated from 1 and 2 above, a score of >100% PD-L1+ is possible.

(b) CD8+ and/or CD68+

The tissue section is scanned at 10× for highest density regions and scored at 20× for at least 3 regions, to obtain an average percent positive Infiltrating Non-Malignant Cells (I-NMC) as a percentage of the TMC of the selected regions.

The score is recorded as actual % positive, Avg. % I-NMC+/TMC.

(3) PD-L1+, CD8, CD68: Non-Malignant Cells in the Stromal Interface Area (NMC-SIA)

The tissue section is evaluated to estimate the number of positive Non-Malignant Cells exhibiting any staining intensity as a percentage of the Stromal Interface Area (SIA). Weak staining in the matrix is considered background staining and only non-malignant cells staining at greater intensities (non-equivocal staining) should be considered positive. Cells in cystic spaces should not be included in the assessment of stromal interface.

Scan at 10× for highest density regions and score at 20× for at least 3 regions to obtain an average percent positive of the Stromal Interface Area.

Scores are recorded as actual % positive, Avg. % NMC-SIA.

The Stromal Interface Area is defined by using a 40× field. On the Philips Viewer, annotate with a 0.190 mm² circle to approximate a 40× field on a microscope (see FIG. 1). Place the center of the circle on the interface between malignant and non-malignant cell populations to obtain approximately ½ field of Malignant Cells. The remaining ½ of field of view is the Stromal Interface Area. Due to tissue heterogeneity and tumor morphology, tumors with no clear invasive margin or multiple tumor margins; wherein a 40× field would contain multiple invasive margins/leading edges; Non-malignant cells in the intervening stroma and stromal cells between malignant cells, falls within the defined Stromal Interface (5).

The inability to easily identify a Stromal Interface at 4×/5× is to be marked as Not Evaluable; 'NE' (e.g. in medullary tumors or tumors with diffuse infiltration pattern). Specimens marked with 'NE' do not preclude the specimen from analysis of parameters (1) and (2).

It is noted here that in certain embodiments, each stain is assessed individually (i.e., CD8 or CD68 slides should not be used to identify non-malignant cells when assessing PD-L1 slide).

Figure 2:
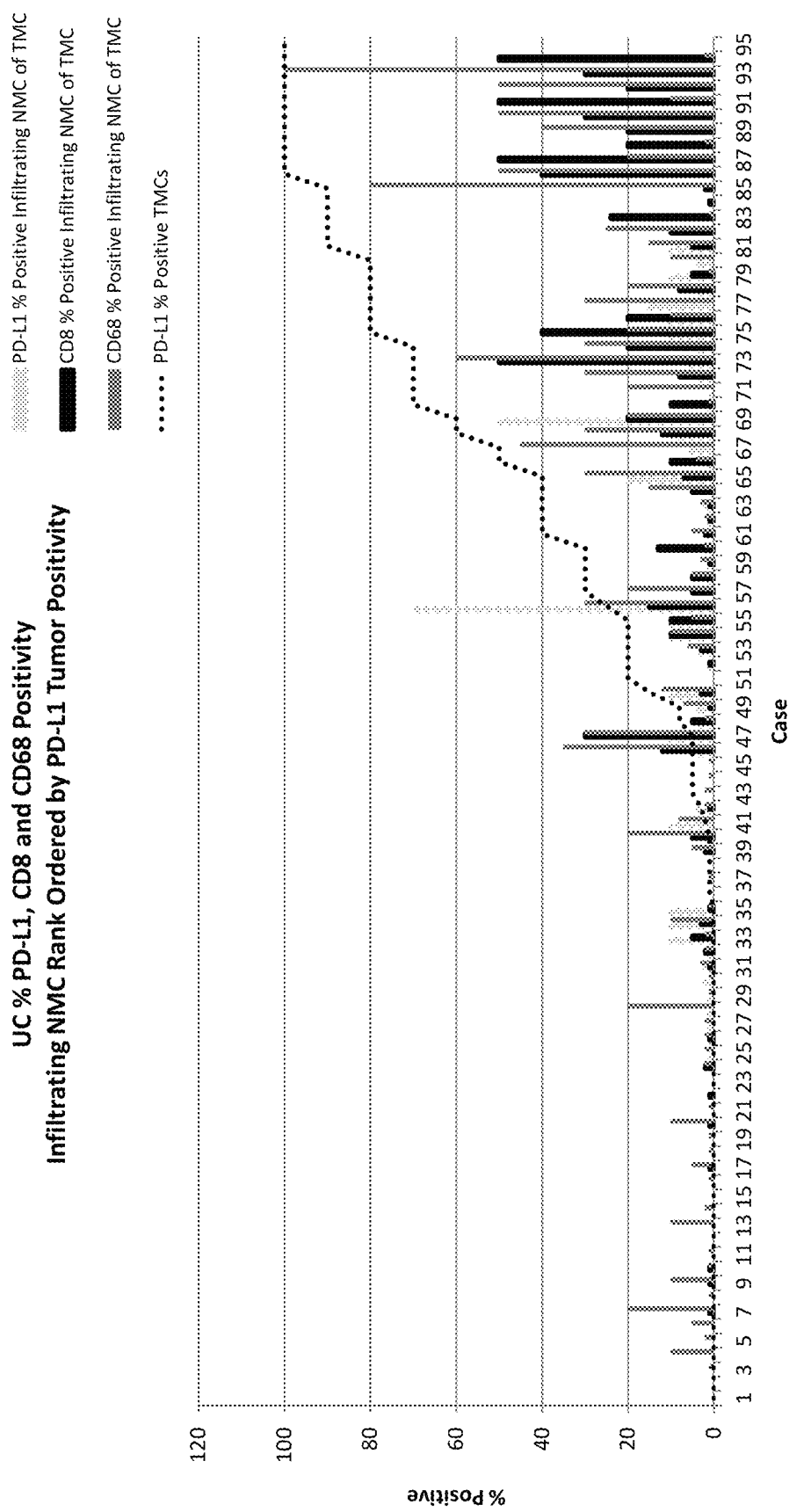
FIG. 2. Infiltrating Non-Malignant Cells in Urothelial Carcinoma, Rank Ordered by PD-L1 Tumor Positivity. Percent PD-L1 positivity of total malignant cells (dotted) rank ordered and compared to PD-L1 (light grey and dotted), CD8 (black) and CD68 (grey) positivity of infiltrating non-malignant cells.

FIG. 2 shows a plot of readouts for infiltrating non-malignant cells (I-NMC) of 95 different subjects having urothelial carcinoma rank ordered by PD-L1 tumor positivity. Percent PD-L1 positivity of total malignant cells (PD-L1% positives TMC; also referred to herein as % MC/TMC) shown in the dotted line; PD-L1 positive I-NMC shown in light grey and dotted bar; CD8 positive I-NMC shown in black bar; and CD68 positive I-NMC shown in grey bar.

Figure 3:
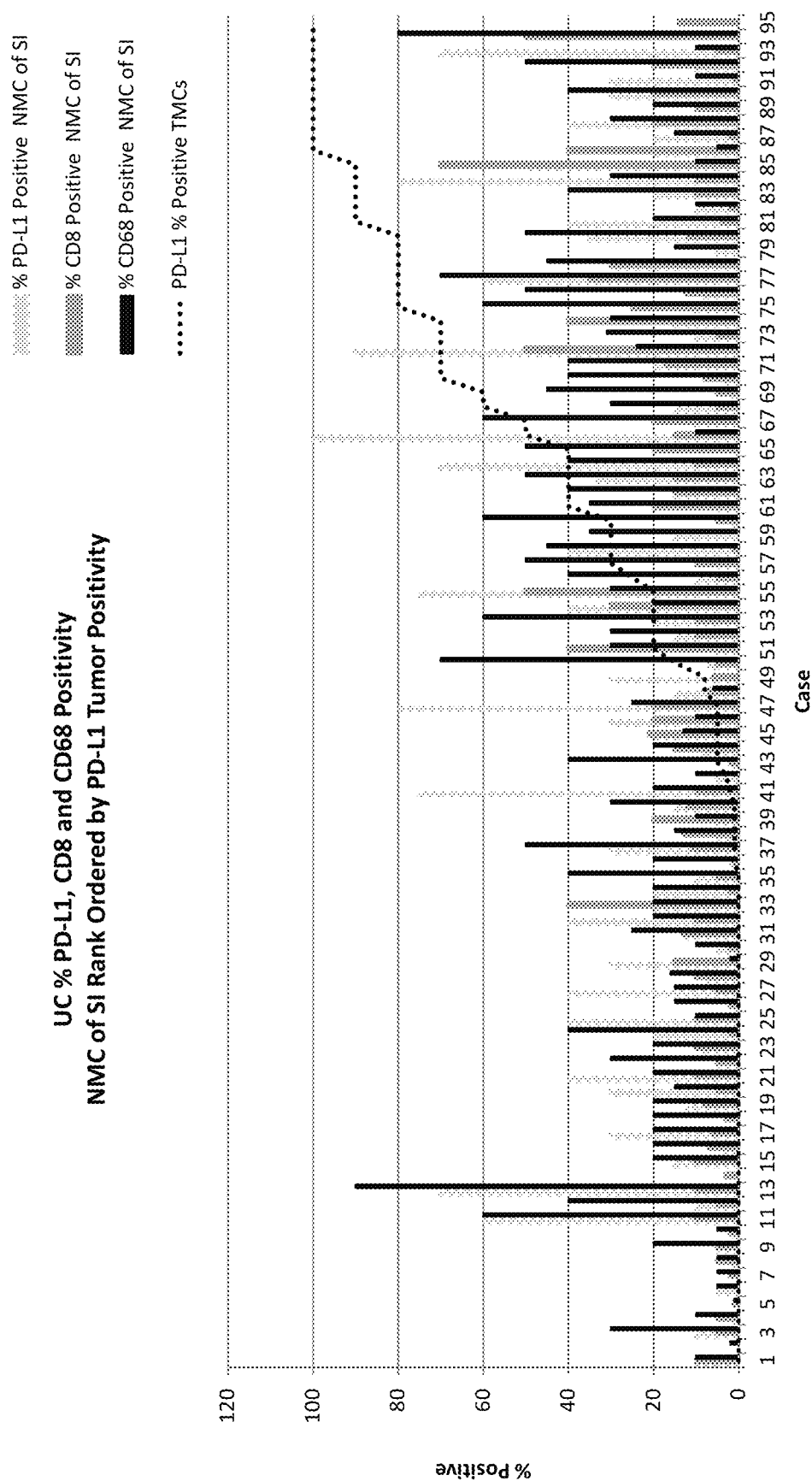
FIG. 3. Non-Malignant Cells of the Stromal Interface in Urothelial Carcinoma, Rank Ordered by PD-L1 Tumor Positivity. Percent PD-L1 positivity of total malignant cells (dotted) rank ordered and compared to PD-L1 (light grey and dotted), CD8 (grey) and CD68 (black) positivity of non-malignant cells of the stromal interface.

FIG. 3 shows the same subjects as in FIG. 2 as a plot of readouts for non-malignant cells of the stromal interface (NMC of SIA) rank ordered by PD-L1 tumor positivity. Percent PD-L1 positivity of total malignant cells (PD-L1% positives TMC; also referred to herein as % MC/TMC) shown in the dotted line; PD-L1 positive NMC of SIA shown in light grey and dotted bar; CD8 positive NMC of SIA shown in grey bar; and CD68 positive NMC of SIA shown in black bar.

Figure 4:
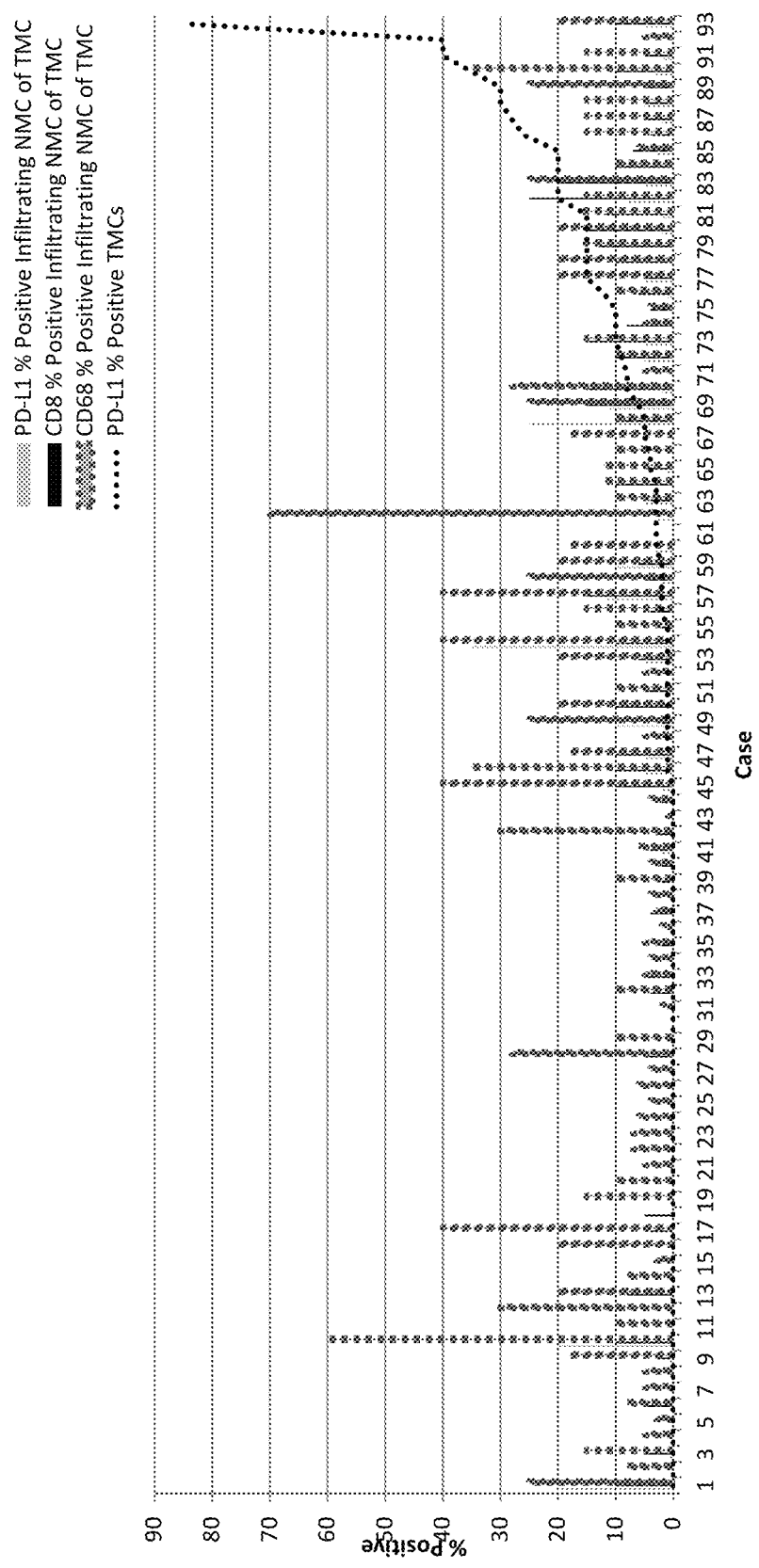
FIG. 4. Infiltrating Non-Malignant Cells in Ovarian Carcinoma, Rank Ordered by PD-L1 Tumor Positivity. Percent PD-L1 positivity of total malignant cells (dotted) rank ordered and compared to PD-L1 (grey), CD8 (black) and CD68 (grey and dotted) positivity of infiltrating non-malignant cells.

FIG. 4 shows a plot of readouts for infiltrating non-malignant cells (I-NMC) of 93 different subjects having epithelial ovarian carcinomas rank ordered by PD-L1 Tumor Positivity. Percent PD-L1 positivity of total malignant cells (PD-L1% positives TMC; also referred to herein as % MC/TMC) shown in the dotted line; PD-L1 positive I-NMC shown in light grey bar; CD8 positive I-NMC shown in black bar; and CD68 positive I-NMC shown in grey and dotted bar.

Figure 5:
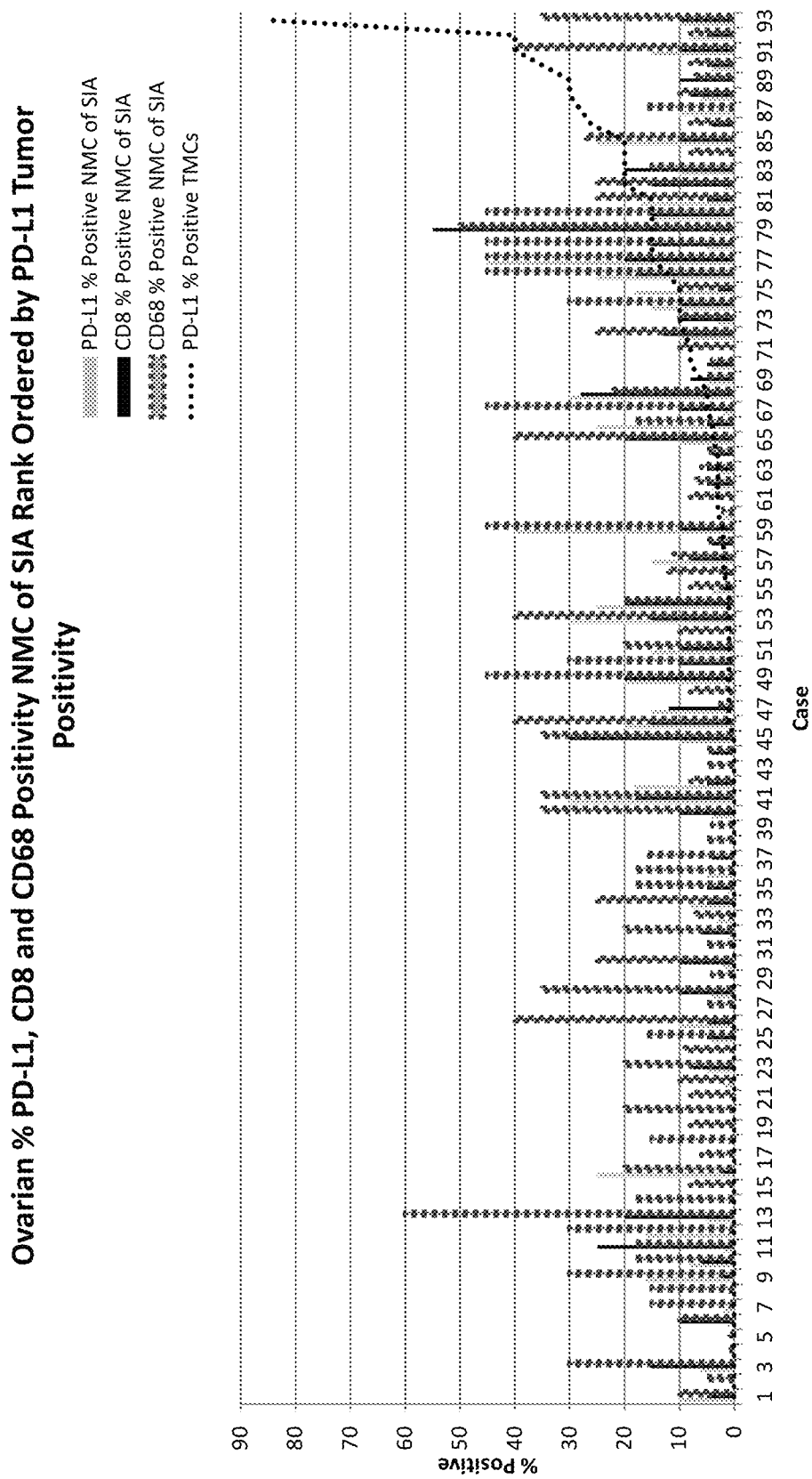
FIG. 5. Non-Malignant Cells of the Stromal Interface in Ocarian Carcinoma, Rank Ordered by PD-L1 Tumor Positivity. Percent PD-L1 positivity of total malignant cells (dotted) rank ordered and compared to PD-L1 (grey), CD8 (black) and CD68 (grey and dotted) positivity of non-malignant cells of the stromal interface.
Figure 6:
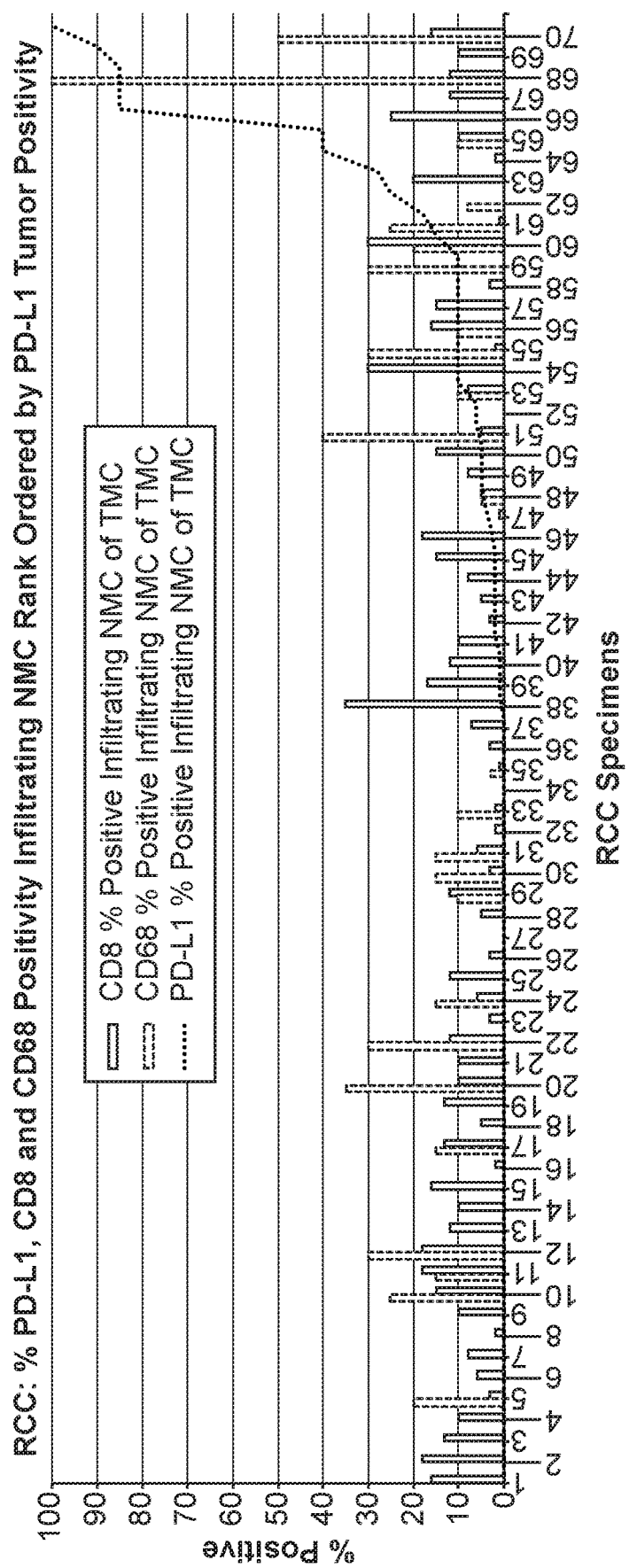
FIG. 6. Infiltrating Non-Malignant Cells in Renal Cell Carcinoma, Rank Ordered by PD-L1 Tumor Positivity. Percent PD-L1 positivity of total malignant cells (dotted) rank ordered and compared to CD8 (black) and CD68 (grey and dotted) positivity of infiltrating non-malignant cells.
Figure 7:
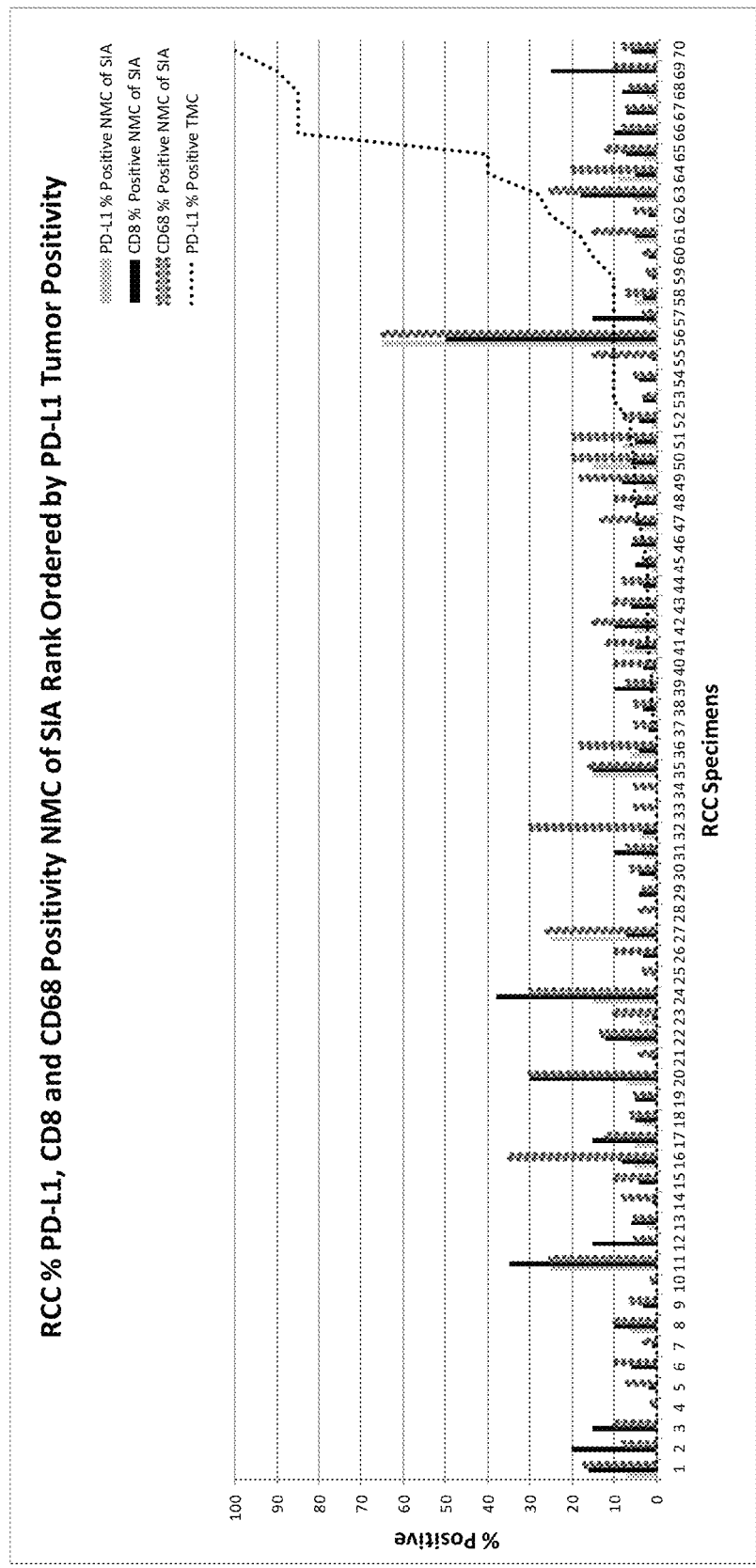
FIG. 7. Non-Malignant Cells of the Stromal Interface in Renal Cell Carcinoma, Rank Ordered by PD-L1 Tumor Positivity. Percent PD-L1 positivity of total malignant cells (dotted) rank ordered and compared to PD-L1 (grey), CD8 (black) and CD68 (grey and dotted) positivity of non-malignant cells of the stromal interface.

FIG. 5 shows a plot of readouts for the same subjects in FIG. 4 with non-malignant cells of the stromal interface area (NMC of SIA) rank ordered by PD-L1 tumor positivity. Percent PD-L1 positivity of total malignant cells (PD-L1% positives TMC; also referred to herein as % MC/TMC) shown in the dotted line; PD-L1 positive NMC of SIA shown in light grey bar; CD8 positive NMC of SIA shown in black bar; and CD68 positive NMC of SIA shown in grey and dotted bar.

Eligibility Scoring

PD-L1:

PD-L1 membrane positivity of tumors cells (MC) can predict clinical response to treatment with anti-PD-L1 immunotherapy. If PD-L1+ is a primary measure of eligibility, subjects with a significant percentage, e.g. >1%; or other defined cut-off deemed to be biologically and/or clinically relevant, of PD-L1+MC are expected to be treatment responders. Intensity of cells staining can also be used to determine eligibility.

PD-L1 positivity of Infiltrating Non-malignant cells (I-NMC) can predict clinical response to treatment with anti-PD-L1 immunotherapy. PD-L1 low expressing or negative subjects, as defined by a biologically and/or clinically relevant cut-off based on malignant/tumor cells, I-NMC expression would be a measure of eligibility. PD-L1 positivity of Non-Malignant cells in the Stromal Interface Area (NMC-SIA) can predict clinical response to treatment with anti-PD-L1 immunotherapy, where the subjects may be MC negative, I-NMC negative, but stromal positive for NMC.

CD8:

CD8 positivity of Infiltrating, Non-Malignant cells can predict clinical response to treatment with anti-PD-L1 immunotherapy. The presence of positive CD8 infiltrating non-malignant cells may be determined to be a measure of eligibility to quantify or describe infiltration, severity, or degree; with or without PD-L1.

CD8 positivity of cells in the Stromal Interface Area can predict clinical response to treatment with anti-PD-L1 immunotherapy as described above for PD-L1 NMC of SIA.

CD68: CD68 positivity of Non-Malignant cells can predict clinical response to treatment with anti-PD-L1 immunotherapy as described above for I-NMC of PD-L1 and CD8.

CD68 positivity of cells in the Stromal Interface Area can predict clinical response to treatment with anti-PD-L1 immunotherapy as described above for PD-L1 and CD8 NMC of SIA.

A combination of the above staining of cells in a tumor can predict clinical response.

A calculated percent positive of stained cells expressed as a ratio/fraction/sum in relationship to at least 1 of the 3 markers is used to quantify expression and predict clinical response. A tiered or conditional method of determining eligibility can require a series of presence or absence of a variation of PD-L1/CD8/CD68. For example, a subject or specimen evaluation can proceed through a series of questions to determine eligibility by way of IF/AND/OR statements to describe positivity of the markers of interest, i.e., IF PD-L1 positive, AND CD8 positive, be eligible for treatment. For example, a subject may be called 'Triple Positive' if positive for 3 markers. Furthermore, subcellular locations or histological compartment classification of either infiltrating or stromal NMC provide additional information to determine an immune signature; an identifiable pattern of expression of the immune markers, to be used in a manner to predict treatment response or outcome. Subcellular/regional/histological compartments may be used to describe ROIs to determine co-localization or localization of MC and NMC positivity. A weighted average can also be applied to the determine eligibility wherein the percent positive of staining cells are captured by intensity and calculated to obtain a proportion to determine eligibility.

Kits

Also provided by this disclosure are kits that provide reagents for analyzing a tissue section(s) for determining the eligibility of a subject having a malignancy for treatment with an anti-PD therapeutic agent according to the methods described herein.

For example, a kit may contain a detectable PD-L1 specific binding agent; a detectable CD8 specific binding agent; a detectable CD68 specific binding agent; and one or more reagents for performing an immunohistochemistry (IHC) staining reaction on a tumor tissue sample from a subject.

The various components of the kit may be present in separate containers or certain compatible components may be precombined into a single container, as desired.

In addition to above-mentioned components, the subject kits may further include instructions for using the components of the kit to practice the subject methods, i.e., instructions for sample analysis, and or instructions for interpreting the results of the test, e.g., for calculating an eligibility score to determine the eligibility of a subject having a malignancy for treatment with an anti-PD therapeutic agent, e.g., an anti-PD-L1 antibody therapy. Such instructions for practicing the subject methods and interpreting the results are generally recorded on a suitable recording medium. For example, the instructions may be printed on a substrate, such as paper or plastic, etc. As such, the instructions may be present in the kits as a package insert, Instructions For Use (IFU), in the labeling of the container of the kit or components thereof (i.e., associated with the packaging or sub-packaging), etc. In other embodiments, the instructions are present as an electronic storage data file present on a suitable computer readable storage medium, e.g., CD-ROM, diskette, memo, etc. In yet other embodiments, the actual instructions are not present in the kit, but means for obtaining the instructions from a remote source, e.g., via the internet, are provided. An example of this embodiment is a kit that includes a web address where the instructions can be viewed and/or from which the instructions can be downloaded. As with the instructions, this means for obtaining the instructions is recorded on a suitable substrate.

REFERENCES

Denardo, D. G., et al. (2011). Leukocyte Complexity Predicts Breast Cancer Survival and Functionally Regulates Response to Chemotherapy. Cancer Discovery, 1(1), 54-67.

Greaves, P., et al. (2012). Expression of FOXP3, CD68, and CD20 at Diagnosis in the Microenvironment of Classical Hodgkin Lymphoma Is Predictive of Outcome. Journal of Clinical Oncology, 31(2), 256-262.

Haas, M., Dimmler, A., Hohenberger, W., Grabenbauer, G. G., Niedobitek, G., & Distel, L. V. (2009). Stromal regulatory T-cells are associated with a favourable prognosis in gastric cancer of the cardia. BMC Gastroenterol BMC Gastroenterology, 9(1), 65.

Hamanishi, J., Mandai, M., Iwasaki, M., Okazaki, T., Tanaka, Y., Yamaguchi, K., . . . Fujii, S. (2007). Programmed cell death 1 ligand 1 and tumor-infiltrating CD8 T lymphocytes are prognostic factors of human ovarian cancer. Proceedings of the National Academy of Sciences, 104(9), 3360-3365.

Helal, T. E., Alla, A. E., Laban, M. A., & Fahmy, R. M. (2004). Immunophenotyping of tumor-infiltrating mononuclear cells in ovarian carcinoma. Pathology & Oncology Research Pathol. Oncol. Res., 10(2), 80-84.

Herbst, R. S., et al. (2014). Predictive correlates of response to the anti-PD-L1 antibody MPDL3280A in cancer patients. *Nature*, 515(7528), 563-567.

Herzog, T., Arguello, D., Reddy, S., & Gatalica, Z. (2015). PD-1, PD-L1 expression in 1599 gynecological cancers: Implications for immunotherapy. Gynecologic Oncology, 137, 204-205.

Kuang, D., Zhao, Q., Peng, C., Xu, J., Zhang, J., Wu, C., & Zheng, L. (2009). Activated monocytes in peritumoral stroma of hepatocellular carcinoma foster immune privilege and disease progression through PD-L1. Journal of Experimental Medicine, 206(6), 1327-1337.

Lyford-Pike, S., et al. (2013). Evidence for a Role of the PD-1:PD-L1 Pathway in Immune Resistance of HPV-Associated Head and Neck Squamous Cell Carcinoma. Cancer Research, 73(6), 1733-1741.

Russell, S., et al. (2013). Immune cell infiltration patterns and survival in head and neck squamous cell carcinoma. Head & Neck Oncology, 5(3), 24-.

Salgado, R., et al. (2014). The evaluation of tumor-infiltrating lymphocytes (TILs) in breast cancer: Recommendations by an International TILs Working Group 2014. Annals of Oncology, 26(2), 259-271.

Sato, E., et al. (2005). Intraepithelial CD8 tumor-infiltrating lymphocytes and a high CD8/regulatory T cell ratio are associated with favorable prognosis in ovarian cancer. *Proceedings of the National Academy of Sciences*, 102 (51), 18538-18543.

Stumpf, M., et al. (2009). Intraepithelial CD8-positive T lymphocytes predict survival for patients with serous stage III ovarian carcinomas: Relevance of clonal selection of T lymphocytes. Br J Cancer British Journal of Cancer, 101(9), 1513-1521.

Taube, J. M., et al. (2014). Association of PD-1, PD-1 Ligands, and Other Features of the Tumor Immune Microenvironment with Response to Anti-PD-1 Therapy. Clinical Cancer Research, 20(19), 5064-5074.

Tumeh, P. C., et al. (2014). PD-1 blockade induces responses by inhibiting adaptive immune resistance. *Nature*, 515 (7528), 568-571.

Varga, A., et al. (2015). Abstract 5510: Antitumor activity and safety of pembrolizumab in patients (pts) with PD-L1 positive advanced ovarian cancer: Interim results from a phase Ib study. Clin Oncol, 33.

Zhang, L., et al. (2003). Intratumoral T Cells, Recurrence, and Survival in Epithelial Ovarian Cancer. *New England Journal of Medicine N Engl J Med*, 348(3), 203-213.

EXEMPLARY EMBODIMENTS

Non-limiting examples of embodiments of certain aspects of the subject disclosure are provided below.

1. A method for determining the eligibility of a subject having a malignancy for treatment with an anti-PD therapeutic agent, the method comprising: determining the percentage PD-L1 positive malignant cells (MC) per total malignant cells (TMC) (% MC/TMC) in a tumor tissue section from the subject; determining a second parameter of a tumor tissue section from the subject, wherein the second parameter is selected from: (i) the percentage of infiltrating non-malignant cells (I-NMC) per TMC (% I-NMC/TMC); and (ii) the percentage of non-malignant cells of the stromal interface area (NMC-SIA) per TMC (% NMC-SIA/TMC); wherein the I-NMC and NMC-SIA are positive for a marker selected from: PD-L1, CD8, CD68, and any combination thereof; wherein the subject is eligible for treatment with an anti-PD therapeutic agent when the ratio of % MC/TMC is greater than 1%.

2. The method of embodiment 1, wherein both the % I-NMC/TMC and % NMC-SIA/TMC are determined.

3. The method of embodiment 1 or 2, wherein the I-NMC are positive for PD-L1, wherein the subject is eligible for treatment with an anti-PD therapeutic agent when % I-NMC/TMC is greater than 0 alone, or greater than or equal to % MC/TMC.

4. The method of any one of embodiments 1 to 3, wherein the I-NMC are positive for CD8, wherein the subject is eligible for treatment with an anti-PD therapeutic agent when % I-NMC/TMC is greater than 0 alone, or greater than or equal to % MC/TMC.

5. The method of any one of embodiments 1 to 4, wherein the I-NMC are positive for CD68, wherein the subject is eligible for treatment with an anti-PD therapeutic agent when % I-NMC/TMC is greater than 0 alone, or greater than or equal to % MC/TMC.

6. The method of any one of embodiments 1 to 5, wherein the NMC-SIA are positive for PD-L1, wherein the subject is eligible for treatment with an anti-PD therapeutic agent when % NMC-SIA/TMC is: greater than 5%; greater than % MC/TMC; and/or greater than % I-NMC/TMC.

7. The method of any one of embodiments 1 to 6, wherein the NMC-SIA are positive for CD8, wherein the subject is eligible for treatment with an anti-PD therapeutic agent when % NMC-SIA/TMC is: greater than 5%; greater than % MC/TMC; and/or greater than % I-NMC/TMC.

8. The method of any one of embodiments 1 to 7, wherein the NMC-SIA are positive for CD68, wherein the subject is eligible for treatment with an anti-PD therapeutic agent when % NMC-SIA/TMC is: greater than 5%; greater than % MC/TMC; and/or greater than % I-NMC/TMC.

9. The method of any preceding embodiment, wherein the PD-L1, CD8 and/or CD68 markers are determined by immunohistochemistry (IHC) staining.

10. The method of embodiment 9, wherein the IHC staining for each of PD-L1, CD8 and/or CD68 is performed on the same tissue section.

11. The method of embodiment 9, wherein the IHC staining for each of PD-L1, CD8 and/or CD68 is performed on separate tissue sections of a single tumor biopsy sample from the subject.

12. The method of any preceding embodiment, wherein the tumor tissue section is a formalin fixed and embedded in paraffin wax (FFPE) tumor tissue section.

13. The method of any preceding embodiment, wherein the malignancy is selected from the group consisting of: renal cell carcinoma, urothelial carcinoma, ovarian carcinoma, myeloma, melanoma, lung cancer, squamous cell carcinoma, gastric cancer, bladder cancer, head and neck cancer, classical Hodgkin's lymphoma, Merkel cell carcinoma, and breast cancer.

14. The method of embodiment 13, wherein the % MC/TMC score is greater than 1%, and % iNMC/TMC and/or % NMC-SIA/TMC is positive.

15. The method of embodiment 14, wherein the iNMC and NMC-SIA are CD8+ or CD68+.

16. The method of any one of embodiments 13 to 15, wherein the cancer is urothelial carcinoma.

17. The method of embodiment 13, wherein the % MC/TMC score is 0, and % iNMC/TMC and/or % NMC-SIA/TMC is positive.

18. The method of any preceding embodiment, wherein the anti-PD therapeutic agent comprises an anti-PD or anti-PD-L1 specific antibody or binding fragment thereof.

19. The method of embodiment 18, wherein the anti-PD therapeutic agent is selected from the group consisting of: Avelumab (MSB0010178C), Nivolumab, Pembrolizumab, BMS-936559, MPDL3280A, Pidilizumab, and MEDI4736.

20. The method of embodiment 19, wherein the anti-PD therapeutic agent is Avelumab.

21. The method of any preceding embodiment, wherein the subject is a human.

22. A kit for determining the eligibility of a subject having a malignancy for treatment with an anti-PD therapeutic agent, comprising: a detectable PD-L1 specific binding agent; a detectable CD8 specific binding agent; a detectable CD68 specific binding agent; and one or more reagents for performing an immunohistochemistry (IHC) staining reaction on a tumor tissue sample from a subject.

A method of treatment is provided. In some embodiments, the method comprises: determining the percentage PD-L1 positive malignant cells (MC) per total malignant cells (TMC) (% MC/TMC) in a tumor tissue section from the subject, and determining a second parameter of a tumor tissue section from the subject, wherein the second parameter is selected from: (i) the percentage of infiltrating non-malignant cells (I-NMC) per TMC (% I-NMC/TMC); and (ii) the percentage of non-malignant cells of the stromal interface area (NMC-SIA) per TMC (% NMC-SIA/TMC); wherein the I-NMC and NMC-SIA are positive for a marker selected from: PD-L1, CD8, CD68, and any combination thereof; and treating the subject with an anti-PD therapeutic agent if the ratio of % MC/TMC is greater than 1%.

It will also be recognized by those skilled in the art that, while the invention has been described above in terms of preferred embodiments, it is not limited thereto. Various features and aspects of the above described invention may be used individually or jointly. Further, although the invention has been described in the context of its implementation in a particular environment, and for particular applications those skilled in the art will recognize that its usefulness is not limited thereto and that the present invention can be beneficially utilized in any number of environments and implementations. Accordingly, the claims set forth below should be construed in view of the full breadth and spirit of the invention as disclosed herein.

What is claimed is:

1. A method for determining the eligibility of a subject having a malignancy for treatment with an anti-PD therapeutic agent, the method comprising:
    determining, by immunohistochemistry (IHC) staining, the percentage of PD-L1 positive malignant cells (MC) per total malignant cells (TMC) (% MC/TMC) in a tumor tissue section from the subject;

determining a second parameter of a tumor tissue section from the subject, wherein the second parameter is selected from:
- (i) the percentage of infiltrating non-malignant cells (I-NMC) per TMC (% I-NMC/TMC); and
- (ii) the percentage of non-malignant cells of the stromal interface area (NMC-SIA) per TMC (% NMC-SIA/TMC);

wherein the I-NMC and NMC-SIA are positive, as determined by IHC staining, for a marker selected from: PD-L1, CD8, CD68, and any combination thereof;

wherein the subject is determined to be eligible for treatment with an anti-PD therapeutic agent when the ratio of % MC/TMC is greater than 1% and either
- (a) the I-NMC are positive for PD-L1 and % I-NMC/TMC is greater than 0 alone, or greater than or equal to % MC/TMC; or
- (b) the NMC-SIA are positive for PD-L1 and % NMC-SIA/TMC is: greater than 5%; greater than % MC/TMC; and/or greater than % I-NMC/TMC, and administering an anti-PD therapeutic agent to a subject determined to be eligible for treatment with said anti-PD therapeutic agent.

2. The method of claim 1, wherein both the % I-NMC/TMC and % NMC-SIA/TMC are determined.

3. The method of claim 1, wherein the I-NMC are positive for CD8, wherein the subject is eligible for treatment with an anti-PD therapeutic agent when % I-NMC/TMC is greater than 0 alone, or greater than or equal to % MC/TMC.

4. The method of claim 1, wherein the I-NMC are positive for CD68, wherein the subject is eligible for treatment with an anti-PD therapeutic agent when % I-NMC/TMC is greater than 0 alone, or greater than or equal to % MC/TMC.

5. The method of claim 1, wherein the NMC-SIA are positive for CD8, wherein the subject is eligible for treatment with an anti-PD therapeutic agent when % NMC-SIA/TMC is: greater than 5%; greater than % MC/TMC; and/or greater than % I-NMC/TMC.

6. The method of claim 1, wherein the NMC-SIA are positive for CD68, wherein the subject is eligible for treatment with an anti-PD therapeutic agent when % NMC-SIA/TMC is: greater than 5%; greater than % MC/TMC; and/or greater than % I-NMC/TMC.

7. The method of claim 1, wherein the IHC staining for each of PD-L1, CD8 and/or CD68 is performed on the same tissue section.

8. The method of claim 1, wherein the IHC staining for each of PD-L1, CD8 and/or CD68 is performed on separate tissue sections of a single tumor biopsy sample from the subject.

9. The method of claim 1, wherein the tumor tissue section is a formalin fixed and embedded in paraffin wax (FFPE) tumor tissue section.

10. The method of claim 1, wherein the malignancy is selected from the group consisting of: renal cell carcinoma, urothelial carcinoma, ovarian carcinoma, myeloma, melanoma, lung cancer, squamous cell carcinoma, gastric cancer, bladder cancer, head and neck cancer, classical Hodgkin's lymphoma, Merkel cell carcinoma, and breast cancer.

11. The method of claim 10, wherein the % MC/TMC score is greater than 1%, and % iNMC/TMC and/or % NMC-SIA/TMC is positive.

12. The method of claim 11, wherein the iNMC and NMC-SIA are CD8+ or CD68+.

13. The method of claim 10, wherein the cancer is urothelial carcinoma.

14. The method of claim 10, wherein the % MC/TMC score is 0, and % iNMC/TMC and/or % NMC-SIA/TMC is positive.

15. The method of claim 1, wherein the anti-PD therapeutic agent comprises an anti-PD or anti-PD-L1 specific antibody or binding fragment thereof.

16. The method of claim 15, wherein the anti-PD therapeutic agent is selected from the group consisting of: Avelumab (MSB0010178C), Nivolumab, Pembrolizumab, BMS-936559, MPDL3280A, Pidilizumab, and MEDI4736.

17. A method for determining the eligibility of a subject having a malignancy for treatment with an anti-PD therapeutic agent, the method comprising:

determining the percentage of PD-L1 positive malignant cells (MC) per total malignant cells (TMC) (% MC/TMC) in a formalin fixed and embedded in paraffin wax (FFPE) tumor tissue section from the subject;

determining a second parameter of the tumor tissue section from the subject, wherein the second parameter is selected from:
- (i) the percentage of infiltrating non-malignant cells (I-NMC) per TMC (% I-NMC/TMC); and
- (ii) the percentage of non-malignant cells of the stromal interface area (NMC-SIA) per TMC (% NMC-SIA/TMC);

wherein the I-NMC and NMC-SIA are positive for a marker selected from: PD-L1, CD8, CD68, and any combination thereof;

wherein the subject is determined to be eligible for treatment with an anti-PD therapeutic agent when the ratio of % MC/TMC is greater than 1% and either
- (a) the I-NMC are positive for PD-L1 and % I-NMC/TMC is greater than 0 alone, or greater than or equal to % MC/TMC; or
- (b) the NMC-SIA are positive for PD-L1 and % NMC-SIA/TMC is: greater than 5%; greater than % MC/TMC; and/or greater than % I-NMC/TMC, and administering an anti-PD therapeutic agent to a subject determined to be eligible for treatment with said anti-PD therapeutic agent.

* * * * *